(12) United States Patent
Roh et al.

(10) Patent No.: US 12,159,715 B2
(45) Date of Patent: *Dec. 3, 2024

(54) SURGICAL EQUIPMENT MONITORING

(71) Applicant: IX Innovation LLC, Seattle, WA (US)

(72) Inventors: Jeffrey Roh, Seattle, WA (US); Justin Esterberg, Mercer Island, WA (US); John Cronin, Jericho, VT (US); Seth Cronin, Essex Junction, VT (US); Michael D'Andrea, Burlington, VT (US)

(73) Assignee: IX Innovation LLC, Seattle, WA (US)

( * ) Notice: Subject to any disclaimer, the term of this patent is extended or adjusted under 35 U.S.C. 154(b) by 150 days.

This patent is subject to a terminal disclaimer.

(21) Appl. No.: 17/898,732

(22) Filed: Aug. 30, 2022

(65) Prior Publication Data
US 2023/0067796 A1 Mar. 2, 2023

Related U.S. Application Data

(63) Continuation of application No. 17/408,417, filed on Aug. 21, 2021, now Pat. No. 11,462,324.

(51) Int. Cl.
| | |
|---|---|
| *G16H 40/67* | (2018.01) |
| *A61B 34/10* | (2016.01) |
| *A61B 34/30* | (2016.01) |
| *G16H 10/60* | (2018.01) |
| *G16H 20/40* | (2018.01) |
| *G16H 40/40* | (2018.01) |
| *A61B 90/00* | (2016.01) |

(52) U.S. Cl.
CPC ............. *G16H 40/67* (2018.01); *A61B 34/10* (2016.02); *A61B 34/30* (2016.02); *G16H 10/60* (2018.01); *G16H 20/40* (2018.01); *G16H 40/40* (2018.01); *A61B 2090/064* (2016.02)

(58) Field of Classification Search
CPC ........ G16H 40/63; G16H 40/67; G16H 40/60; G16H 10/60; G16H 20/40; G16H 40/40; A61B 34/00; A61B 34/30; A61B 34/32
See application file for complete search history.

(56) References Cited

U.S. PATENT DOCUMENTS

| | | | |
|---|---|---|---|
| 10,299,868 | B2 | 5/2019 | Tsuboi et al. |
| 11,462,324 | B1 | 10/2022 | Roh et al. |
| 2019/0206561 | A1 | 7/2019 | Shelton, IV et al. |
| 2019/0357873 | A1 | 11/2019 | Uebler |
| 2020/0331145 | A1 | 10/2020 | Tanaka et al. |

FOREIGN PATENT DOCUMENTS

WO      2017098504      6/2017

*Primary Examiner* — John R Downey
(74) *Attorney, Agent, or Firm* — Perkins Coie LLP

(57) ABSTRACT

Methods, systems, and apparatus for surgical equipment monitoring are disclosed. In some embodiments, an electronic health records database and a database of surgical tools is provided. At least one sensor and at least one surgical tool are used before, during, or after a surgical procedure. The at least one sensor associated with the at least one surgical tool is monitored for at least one parameter. The monitored data is compared to the expected value of that parameter for the current step in the surgical procedure from the surgical tools database. In response to determining a potential surgical complication, the system generates a notification indicating the potential surgical complication.

20 Claims, 8 Drawing Sheets

| Procedure | Device | Event Type | Patient Problem | Description |
|---|---|---|---|---|
| Appendiceal mesentery | ABC brand Linear Cutting Stapler model 123 | Malfunction | Blood Loss | The ABC brand linear cutting stapler model 123 with used on the appendiceal mesentery failed to control bleeding. Cautery and a clip were required to control bleeding from the staple line. Ebl was still minimal and there was no harm to the patient but the stapler did not function as it should. |
| One anastomosis gastric bypass | XYZ brand Circular Stapler model 456 | Malfunction | No signs or symptoms | The XYZ brand circular stapler model 456 malfunctioned during use on a gastric bypass case. The staple line was complete and md needed to oversew the anastomosis to prevent a leak. The tech, who is very well versed in the use/function of the XYZ model 123, also stated it was hard to load the device with the surgical staples. |

*FIG. 5*

| Surgical Tool | XYZ brand Circular Stapler model 456 |
|---|---|
| Procedures | ApplicationsModel456.dat |
| Current Procedures | One anastomosis gastric bypass |
| Sensors | Force transducers (2) Optical sensor (1) |
| Expected Measure - Force Transducers | 2lb of pressure |
| High Risk Threshold | >25% variance between sensors |
| Low Risk Threshold | >50% variance between sensors in 3/10 or adjacent staples |
| Expected Measure - Optical | |

*FIG. 6A*

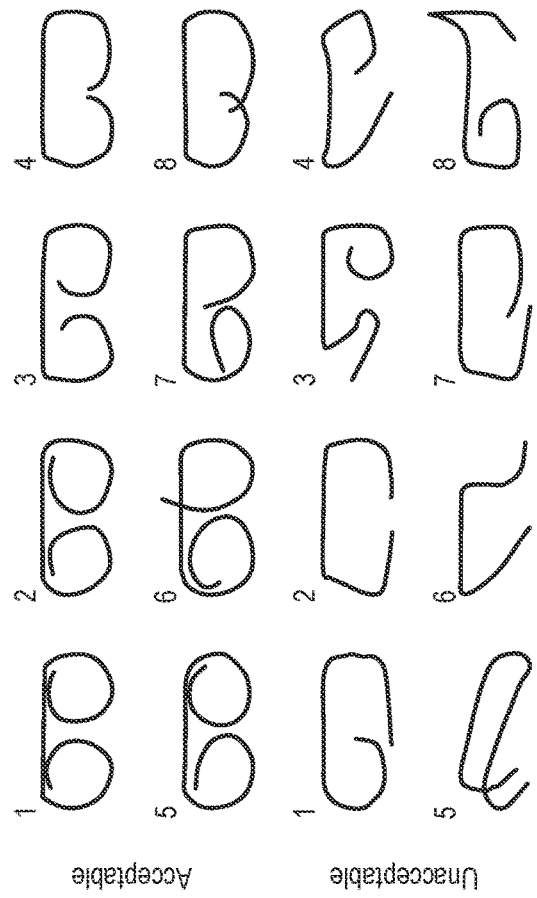

*FIG. 6B*

SURGICAL EQUIPMENT MONITORING

CROSS-REFERENCE TO RELATED APPLICATION

This application is a continuation of U.S. patent application Ser. No. 17/408,417, filed Aug. 21, 2021, which is incorporated herein by reference in its entirety.

TECHNICAL FIELD

The present disclosure is generally related to automated and robotic surgical procedures and specifically to systems and methods for surgical equipment monitoring.

BACKGROUND

More than 200 million surgeries are performed worldwide each year and recent reports reveal that adverse event rates for surgical conditions remain unacceptably high, despite traditional patient safety initiatives. Adverse events resulting from surgical interventions can be related to errors occurring before or after the procedure as well as technical surgical errors during the operation. For example, adverse events can occur due to (i) breakdown in communication within and amongst the surgical team, care providers, patients, and their families; (ii) delay in diagnosis or failure to diagnose; and (iii) delay in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the healthcare team. However, conventional methods are typically insufficient to prevent surgical errors and adverse events during surgery.

BRIEF DESCRIPTION OF THE DRAWINGS

FIG. 5 is a table illustrating an example manufacturer and user facility device experience (MAUDE) database, in accordance with one or more embodiments.

FIG. 6A is a table illustrating an example surgical tools database, in accordance with one or more embodiments.

FIG. 6B illustrates an example set of acceptable and unacceptable staple forms, in accordance with one or more embodiments.

DETAILED DESCRIPTION

Figure 1:
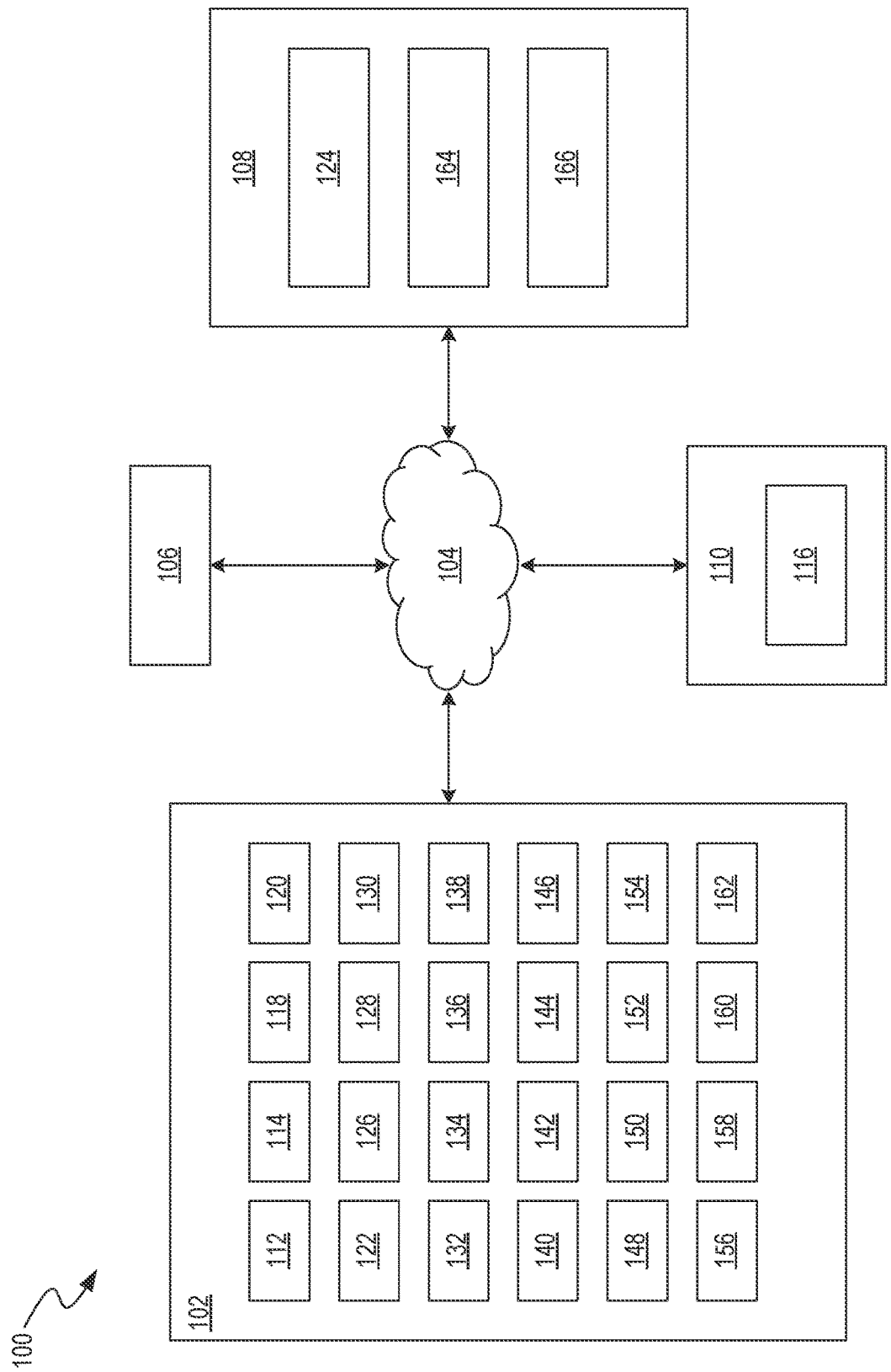
FIG. 1 is a block diagram illustrating an example system for surgical equipment monitoring, in accordance with one or more embodiments.

Embodiments of the present disclosure will be described more thoroughly from now on with reference to the accompanying drawings. Like numerals represent like elements throughout the several Figures, and in which example embodiments are shown. However, embodiments of the claims can be embodied in many different forms and should not be construed as limited to the embodiments set forth herein. The examples set forth herein are non-limiting examples and are merely examples, among other possible examples.

A 1999 study by the Institute of Medicine found that up to 98,000 patients die each year in the United States due to hospitals' mistakes. A 2010 study by the Office of Inspector General for Health and Human Services determined that 180,000 patients on Medicare died due to poor hospital care. In 2013, the Journal of Patient Safety estimated that number to be greater, with between 210,000 and 440,000 patients who suffered some preventable harm during hospital care contributing to their death. Such numbers make medical error the third leading cause of death in America after heart disease and cancer. A global study in 2008 by the World Health Organization estimated that at least 7 million people suffer from surgical complications each year, with at least a million of those resulting in death.

In 2008, the World Health Organization codified guidelines for safe surgery in the form of a 19-item surgical checklist. While the checklist was shown to reduce complications by 35%, and deaths from complications by more than 47%, failure to adhere to these WHO standards occurs between 6% and 20% of all operations in the United States. Equipment misuse or malfunction contributes significantly to these surgical complication rates. For example, according to the U.S. Food and Drug Administration, surgical stapler complications occurred in 98,404 surgeries between 2011 and 2018, with those malfunctions resulting in 11,181 injuries and 412 deaths.

This document presents methods, systems, and apparatus for surgical equipment monitoring. Advanced surgical systems include many different types of medical equipment to monitor and anesthetize a patient, assist a surgeon in performing surgical procedures, and maintain an environment of an operating room. The present disclosure is generally related to surgical equipment, preventing surgical complications, and specifically to systems and methods for mitigating surgical complications related to surgical equipment. In some embodiments, an electronic health records database and a database of surgical tools are provided. At least one sensor and at least one surgical tool are used before, during, or after a surgical procedure. The at least one sensor associated with the at least one surgical tool is monitored for at least one parameter. The monitored data is compared to the expected value of that parameter for the current step in the surgical procedure from the surgical tools database. In response to determining a potential surgical complication, the system generates a notification indicating the potential surgical complication. In some embodiments, the methods address surgical equipment issues that could result in potential surgical complications. The systems disclosed monitor surgical equipment to identify potential malfunctions or misuse during a surgical procedure to mitigate issues before complications could arise.

The advantages and benefits of the methods, systems, and apparatus for surgical equipment monitoring disclosed herein include compatibility with best practice guidelines for surgery in an operating room, e.g., from regulatory bodies and professional standards organizations such as the Association of Surgical Technologists. The robotic surgery technologies disclosed offer valuable enhancements to medical or surgical processes through improved precision, stability, and dexterity. The disclosed methods relieve medical personnel from routine tasks and make medical procedures safer and less costly for patients. The embodiments disclosed can also perform more accurate surgery and address the use of dangerous substances. The adoption of robotic systems, according to the embodiments disclosed herein, provides several additional benefits, including efficiency and speed improvements, lower costs, and more accuracy. The equipment tracking system integrated into the disclosed embodiments offers advantages, such as no line of sight required, read multiple radio frequency identification (RFID) objects at once, scan at a distance, and flexibility. The advantages offered by the surgical tower according to the embodiments disclosed herein are smaller incisions, less pain, lower risk of infection, shorter hospital stays, quicker recovery time, less scarring, and reduced blood loss. The advantages of the convolutional neural network (CNN) used for machine learning in the disclosed embodiments include the obviation of feature extraction and the use of shared weight in convolutional layers, which means that the same filter (weights bank) is used for each node in the layer; this both reduces memory footprint and improves performance.

Methods, apparatus, and systems for surgical equipment monitoring are disclosed. In some embodiments, the methods address surgical equipment issues that could result in potential surgical complications. The systems disclosed monitor surgical equipment to identify potential malfunctions or misuse during a surgical procedure to mitigate issues before complications could arise.

In some embodiments, an electronic health records database and a database of surgical tools are provided. At least one sensor and at least one surgical tool are used before, during, or after a surgical procedure. The at least one sensor associated with the at least one surgical tool is monitored for at least one parameter. The monitored data is compared to the expected value of that parameter for the current step in the surgical procedure from the surgical tools database. In response to determining a potential surgical complication, the system generates a notification indicating the potential surgical complication.

These and other aspects, features, and implementations can be expressed as methods, apparatus, systems, components, program products, means, or steps for performing a function, and in other ways.

FIG. 1 is a block diagram illustrating an example system 100 for surgical equipment monitoring, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The system 100 is implemented using the components of the example computer system 300 illustrated and described in more detail with reference to FIG. 3. Likewise, embodiments of the system 100 can include different and/or additional components, or be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or outpatient surgery center.

In some embodiments, the system 100 includes one or more medical or surgical patient monitors 112. The monitors 112 can include a vital signs monitor (a medical diagnostic instrument), which can be a portable, battery powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiologic parameters of a patient, wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or SpO2 monitor, which is a plethysmograph or any instrument that measures variations in the size of an organ or body part of the patient on the basis of the amount of blood passing through or present in the part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end tidal $CO_2$ monitor or capnography monitor used for measurement of the level of carbon dioxide (referred to as end tidal carbon dioxide, ETCO2) that is released at the end of an exhaled breath. An end tidal CO2 monitor or capnography monitor is widely used in anesthesia and intensive care. ETCO2 can be calculated by plotting expiratory CO2 with time. Further, ETCO2 monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end tidal CO2 monitor can be configured as side stream (diverting) or mainstream (non-diverting). A diverting end tidal CO2 monitor transports a portion of a patient's respired gases from the sampling site to the end tidal CO2 monitor while a non-diverting end tidal CO2 monitor does not transport gas away. Also, measurement by the end tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in the artery, used in the operating room 102) for measurement. The non-invasive method (referred to as a sphygmomanometer) works by measurement of force exerted against arterial walls during ventricular systole (i.e., systolic blood pressure occurs when the heart beats and pushes blood through the arteries) and ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate, which is the rate at which breathing occurs, and is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can bring a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on the skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia where the heart rate becomes faster and bradycardia where the heart rate becomes slower), coronary heart disease, heart attacks, or cardiomyopathy. The instrument used for measurement of the electrocardiogram is called an electrocardiograph which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and sensorimotor cortex, which helps in guiding the surgeon during dissection. Electrophysiological modalities employed in neuromonitoring are an extracellular single unit and local field potential (LFP) recordings, somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP), the electrical signals elicited by the brain and the spinal cord in response to sensory stimulus or touch. SSEP is used for intraoperative neurophysiological monitoring in spinal surgeries. The measurements are reliable, which allow for continuous monitoring during a surgical procedure. The sensor stimulus commonly given to the organs can be auditory, visual, or somatosensory SEPs and applied on the skin, peripheral nerves of the upper limb, lower limb, or scalp. The stimulation technique can be mechanical, electrical (provides larger and more robust responses), or intraoperative spinal monitoring modality.

In some embodiments, the monitors 112 provide electromyography (EMG), the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation, and does not perform external stimulation. Spontaneous EMG is recorded by the insertion of a needle electrode. Triggered EMG refers to the recording of myoelectric signals during stimulation of the target site such as pedicle screws with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end-effectors, cameras mounted to the ceiling or other surface above the surgical theater, or cameras mounted on a tripod or other independent mounting device. In some embodiments, the cameras are body worn by a surgeon or other surgical staff, the cameras are incorporated into a wearable device, such as an augmented reality device like Google Glass, or the cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by performing a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. The doctor moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgeon makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals over long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors comprise a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or light-emitting diodes (LEDs). Surgical lights 122 include sterilizable handles which allow the surgeon to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and is widely used can be procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can be designed as an outer sleeve and an inner sleeve that telescopingly or slidably engages with one another. When a telescope is used to operate on the abdomen, the procedure is called laparoscopy. The surgical tower 128 typically includes access to a variety of surgical tools, such as, for example, electrocautery, radiofrequency, lasers, sensors, etc.

In some embodiments, radiofrequency (RF) is used in association with MIS devices. The RF can be used for the treatment of skin by delivering it to the skin through a minimally invasive tool (e.g., fine needles) which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels which are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes: monopolar or bipolar. The electrocautery instrument 130 can consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing better incision quality than with existing surgical tools and minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of tool-tissue interaction forces. During MIS, the field of view and workspace of tools are compromised due to the indirect access to the anatomy and lack of the surgeon's hand-eye coordination. The sensors 134 provide a tactile sensation to the surgeon by providing information of shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, magnetic resonance imaging (MRI), ultrasound, endoscopy, elastography, tactile imaging, thermography, medical photography, and nuclear medicine, e.g., positron emission tomography (PET). Some factors which can drive the market are cost and clinical advantages of medical imaging modalities, a rising share of aging populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes. Some of the applications where MRI can be used can be brain/spinal cord anomalies, tumors in the body, breast cancer screening, joint injuries, uterine/pelvic pain detection, or heart problems. For the creation of the image by an MRI instrument, magnetic resonance is produced by powerful magnets which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI can be more widely suited for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses computed tomography imaging (CT) that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"—of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer which produces sound waves and sends them into the body. The sound waves that are reflected are converted into electrical signals which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgeons in the placement of specialized surgical instruments and implants. The patient images are taken to guide the physician before or during the medical procedure. The stereotactic navigation system 138 includes a camera having infrared sensors to determine the location of the tip of the probe being used in the surgical procedure. This information is sent in real-time so that the surgeons have a clear image of the precise location of where they are working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient as well as filters out expiratory carbon dioxide. The anesthesiology machine 140 can perform functions such as providing oxygen (02), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetic gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform, flex, or extend individual components of the platform, or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a postoperative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions which are suitable for operation; protect patient from being chilled; and be prepared to meet any emergency.

In some embodiments, the system 100 includes a Jackson frame 144 (or Jackson table), which refers to a frame or table which is designed for use in spine surgeries and can be used in a variety of spinal procedures in supine, prone, or lateral positions in a safe manner. Two peculiar features of the Jackson table 144 are no central table support and an ability to rotate the table through 180°. The Jackson table 144 is supported at both ends which keeps the whole of the table free. This allows the visualization of trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (also referred to as a Bair). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets which cover the patient. The blanket can be designed to use pressure points on the patient's body to prevent heat from reaching areas at risk for pressure sores or burns. The blanket can also include drain holes where fluid passes through the surface of the blanket to linen underneath which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The SCD 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors which can contribute to poor quality in the environment of the operating room 102 are temperature, ventilation, and humidity, and those conditions can lead to profound effects on the health and work productivity of people in the operating room 102. As an example: surgeons prefer a cool, dry climate since they work in bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and the imaging system 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, single large diffuser (based on laminar diffuser flow) or High-Efficiency Particulate Air filter. A High-Efficiency Particulate Air filter (HEPA filter) protects from infection and contamination by a filter which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system which controls the muscles). A major percentage of orthopedic tools are made of plastic. The orthopedic tools can be divided into the following specialties: hand and wrist, foot and ankle, shoulder and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., the Thomas splint and the Voskoboinikova apparatus. A corrective tool refers to a tool designed to gradually correct a deformity, e.g., corsets, splints, orthopedic footwear, insoles, and other devices to correct abnormal positions of the foot. A compression-distraction tool refers to a tool designed to correct acquired or congenital deformities of the extremities, e.g., curvature, shortening, and pseudarthrosis such as Gudushauri. A fixation tool can be an internal fixation tool (e.g., screws, plates) or external fixation tool (for the radius, tibia fracture fixation). The orthopedic tools can be bone-holding forceps, drill bits, nail pins, hammer, staple, etc.

In some embodiments, the tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1,000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can comprise a physical drill, power cord, electronically motorized bone drill, or rotating bone shearing incision work unit.

In some embodiments, the tools 154 include a scalpel for slicing, cutting, or osteotomy of bone during orthopedic procedures. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures), or a sterile, surgical thread, are used to repair cuts or lacerations and are used to close incisions or hold body tissues together after a surgery or an injury. Stitches can involve the use of a needle along with an attached thread. Stitches can be of type absorbable (the stitches automatically break down harmlessly in the body over time without intervention) and non-absorbable (the stitches do not automatically break down over time and must be manually removed if not left indefinitely). Stitches can be based on material monofilament, multifilament, and barb. Stitches can be classified based on size. Stitches can be based on material synthetic and natural. Stitches can be based on coating coated and un-coated.

In some embodiments, the tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, tools, or objects, is used to implement or achieve an operation or activity. Medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as sensor/transducer, signal conditioner, display, data storage unit, etc. In some embodiments, the medical equipment includes a sensor to receive a signal from a measurand/patient; a transducer for converting one form of energy to electrical energy; a signal conditioner such as an amplifier, filter, etc., to convert the output from the transducer into an electrical value; a display to provide a visual representation of the measured parameter or quantity; and a storage system to store data which can be used for future reference. The medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. The ventilator is required when a person is not able to breathe on their own. The ventilator can perform a function of gently pushing air into the lungs (like lungs when they are working) and allows it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc. The ventilator can include a gas delivery system, power source, control system, safety feature, gas filter, and monitor.

In some embodiments, the machine 156 is a continuous positive airway pressure (CPAP) machine used for the treatment of sleep apnea disorder in a patient. Sleep apnea refers to a disorder in which breathing repeatedly stops and starts while a patient is sleeping, often because the throat/ airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor which generates a continuous stream of pressurized air which travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs the oxygen. This helps the patient to not wake up to resume breathing. The CPAP instrument can have a nasal pillow mask, nasal mask, or full mask. The CPAP instrument can comprise a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or operating room 102. The consumables 158 can include gloves, gowns, masks, syringes, needles, sutures, staples, tubing, catheters, or adhesives for wound dressing, in addition to other tools needed by doctors and nurses to provide care. Depending on the device, mechanical testing can be carried out in tensile, compression or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robotic systems, and hospital and pharmacy robotic systems. Robotic surgeries are performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as radio frequency identification (RFID), used to tag an instrument with an electronic tag and track it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. RFID can be very short for low frequency, high frequency, or ultra-high frequency. Managing and locating important assets is a key challenge for tracking medical equipment. Time spent searching for critical equipment can lead to expensive delays or downtime, missed deadlines and customer commitments, and wasted labor. The problem has been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source, and a transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light illuminated and image seen with the microscope 116 is two-dimensional), dissection or stereoscope (light illuminated and image seen with the microscope 116 is three-dimensional), confocal (laser-illuminated and image seen with the microscope 116 is on a digital computer screen), scanning electron (SEM) (electron illuminated and image seen with the microscope 116 is in black and white), or transmission electron microscope (TEM) (electron illuminated and image seen with the microscope 116 is the high magnification and high resolution).

The system 100 includes an electronic health records (EHR) database 106 that contains patient records. The EHR are a digital version of patients' paper charts. The EHR database 106 can contain more information than a traditional patient chart, including, but not limited to, a patient's medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected and stored systematically over time. The EHR database 106 can include demographics, medical history, history of present illness (HPI), progress notes, problems, medications, vital signs, immunizations, laboratory data, or radiology reports.

Software (in memory 164) operating on the console 108 or implemented on the example computer system 300 (e.g., the instructions 304, 308 illustrated and described in more detail with reference to FIG. 3) is used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computer device, such as a server, computer, tablet, smartphone, smart speaker, etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a greater density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitors 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, better image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR database 106 are communicatively coupled to the equipment in the operating room 102 by a direct connection, such as Ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

In some embodiments, the console 108 or the system 10 uses quantum computing. Quantum computing refers to a computational device or method that utilizes properties of quantum states defined by quantum mechanics such as superposition, entanglement, etc., to perform computations. Quantum devices utilize qubits which are the quantum equivalent to bits in a classical computing system. Qubits include at least two quantum states or probable outcomes. These outcomes, combined with a coefficient representing the probability of each outcome, describe the possible states, or bits of data, which can be represented by the qubits according to the principle of quantum superposition. These states can be manipulated which can shift the probability of each outcome or additionally add additional possible outcomes to perform a calculation, the final state of which can be measured to achieve a result.

Quantum computing provides significant benefits in the areas of encryption and the simulation of natural systems. Encryption is aided by the uncertain nature of quantum computing in that data is represented by an indeterminate state of probable outcomes, therefore making decryption virtually impossible. The simulation of natural systems, such as chemical and biological interactions, benefit from the fact that the nature of quantum computing is the same as the systems being simulated. In medical fields, quantum computing shows great promise for drug discovery and simulating the interaction of drugs with biologic systems, however, the same technology can be used to predict the interaction of a biologic system with an implanted device, preventing rejection of an implant by a patient's body, long term function of an implant, and potentially the reaction of a patient to a surgical procedure during a simulation before a procedure or actively during a procedure.

Figure 2:
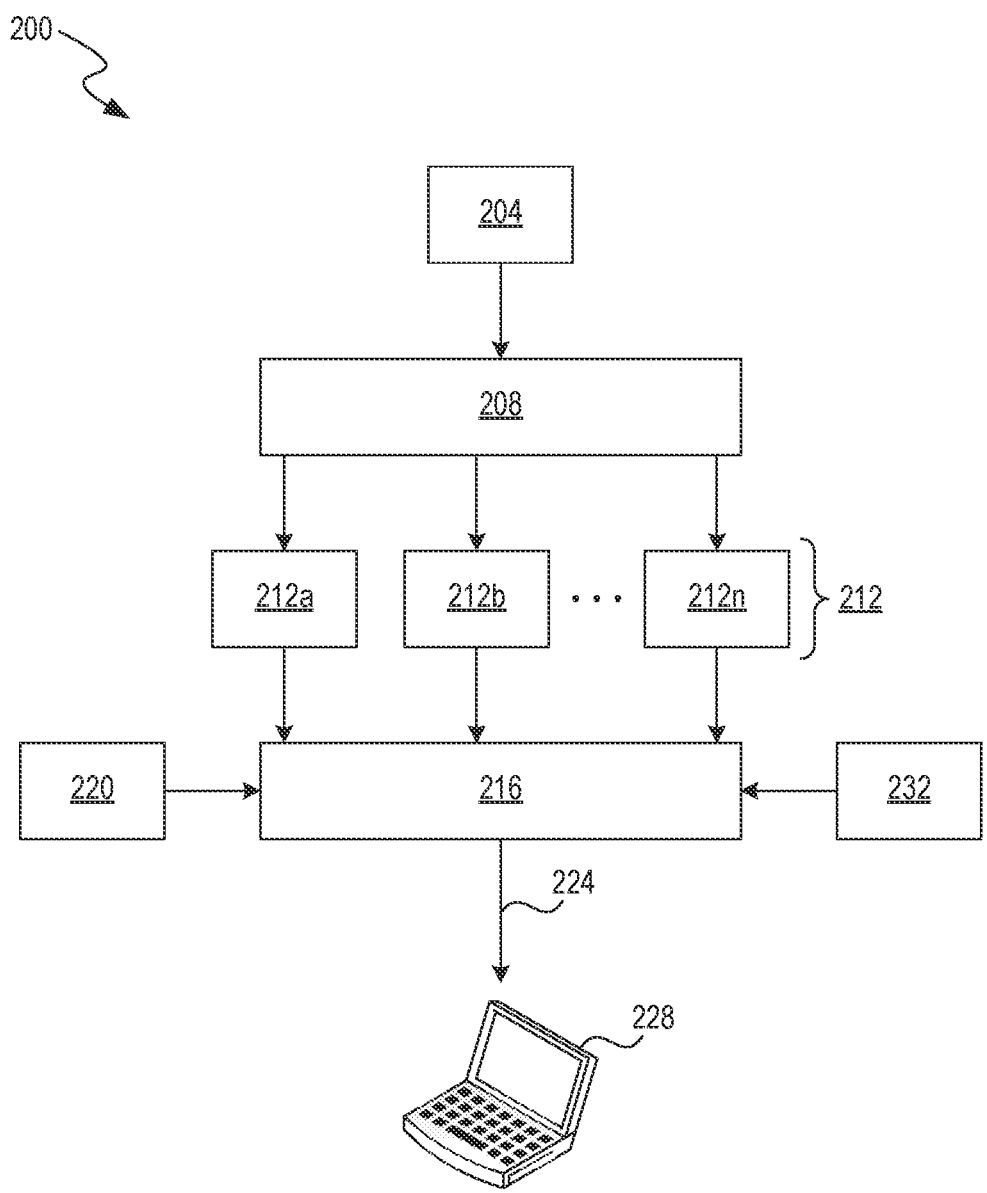
FIG. 2 is a block diagram illustrating an example machine learning system for surgical equipment monitoring, in accordance with one or more embodiments.

FIG. 2 is a block diagram illustrating an example machine learning system 200 for surgical equipment monitoring, in accordance with one or more embodiments. The machine learning system 200 is implemented using components of the example computer system 300 illustrated and described in more detail with reference to FIG. 3. For example, the machine learning system 200 can be implemented on the console 108 using instructions programmed in the memory 164 illustrated and described in more detail with reference to FIG. 1. Likewise, embodiments of the machine learning system 200 can include different and/or additional components, or be connected in different ways. The machine learning system 200 is sometimes referred to as a machine learning module.

The machine learning system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212a, 212b, . . . , 212n. The feature extraction module 208 reduces the redundancy in the input data 204, e.g., repetitive data values, to transform the input data 204 into the reduced set of features 212, e.g., feature 212a, feature 212b, and feature 212n. The feature vector 212 contains the relevant information from the input data 204, such that events or data value thresholds of interest can be identified by a machine learning model 216 by using this reduced representation. In some example embodiments, the following dimensionality reduction techniques are used by the feature extraction module 208: independent component analysis, Isomap, Kernel PCA, latent semantic analysis, partial least squares, principal component analysis, multifactor dimensionality reduction, nonlinear dimensionality reduction, Multilinear Principal Component Analysis, multilinear subspace learning, semidefinite embedding, autoencoder, and deep feature synthesis.

In alternative embodiments, the machine learning model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the machine learning system 200. For example, the machine learning model 216 can use a cascade of multiple layers of nonlinear processing units for implicit feature extraction and transformation. Each successive layer uses the output from the previous layer as input. The machine learning model 216 can thus learn in supervised (e.g., classification) and/or unsupervised (e.g., pattern analysis) modes. The machine learning model 216 can learn multiple levels of representations that correspond to different levels of abstraction, wherein the different levels form a hierarchy of concepts. In this manner, the machine learning model 216 can be configured to differentiate features of interest from background features.

In alternative example embodiments, the machine learning model 216, e.g., in the form of a convolutional neural network (CNN), generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker, etc., implemented using components of the example computer system 300 illustrated and described in more detail with reference to FIG. 3. In some embodiments, the steps performed by the machine learning system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted region of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The machine learning model 216 can be a CNN that includes both convolutional layers and max pooling layers. The architecture of the machine learning model 216 can be "fully convolutional," which means that variable sized sensor data vectors can be fed into it. For all convolutional layers, the machine learning model 216 can specify a kernel size, a stride of the convolution, and an amount of zero padding applied to the input of that layer. For the pooling layers, the machine learning model 216 can specify the kernel size and stride of the pooling.

In some embodiments, the machine learning system 200 trains the machine learning model 216, based on the training data 220, to correlate the feature vector 212 to expected outputs in the training data 220. As part of the training of the machine learning model 216, the machine learning system 200 forms a training set of features and training labels by identifying a positive training set of features that have been determined to have a desired property in question, and, in some embodiments, forms a negative training set of features that lack the property in question.

The machine learning system 200 applies machine learning techniques to train the machine learning model 216, that when applied to the feature vector 212, outputs indications of whether the feature vector 212 has an associated desired property or properties, such as a probability that the feature vector 212 has a particular Boolean property, or an estimated value of a scalar property. The machine learning system 200 can further apply dimensionality reduction (e.g., via linear discriminant analysis (LDA), principal component analysis (PCA), or the like) to reduce the amount of data in the feature vector 212 to a smaller, more representative set of data.

The machine learning system 200 can use supervised machine learning to train the machine learning model 216, with feature vectors of the positive training set and the negative training set serving as the inputs. In some embodiments, different machine learning techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The machine learning system 200 applies the trained machine learning model 216 to the features of the validation set 232 to quantify the accuracy of the machine learning model 216. Common metrics applied in accuracy measurement include: Precision and Recall, where Precision refers to a number of results the machine learning model 216 correctly predicted out of the total it predicted, and Recall refers to a number of results the machine learning model 216 correctly predicted out of the total number of features that had the desired property in question. In some embodiments, the machine learning system 200 iteratively re-trains the machine learning model 216 until the occurrence of a stopping condition, such as the accuracy measurement indication that the machine learning model 216 is sufficiently accurate, or a number of training rounds have taken place.

Figure 3:
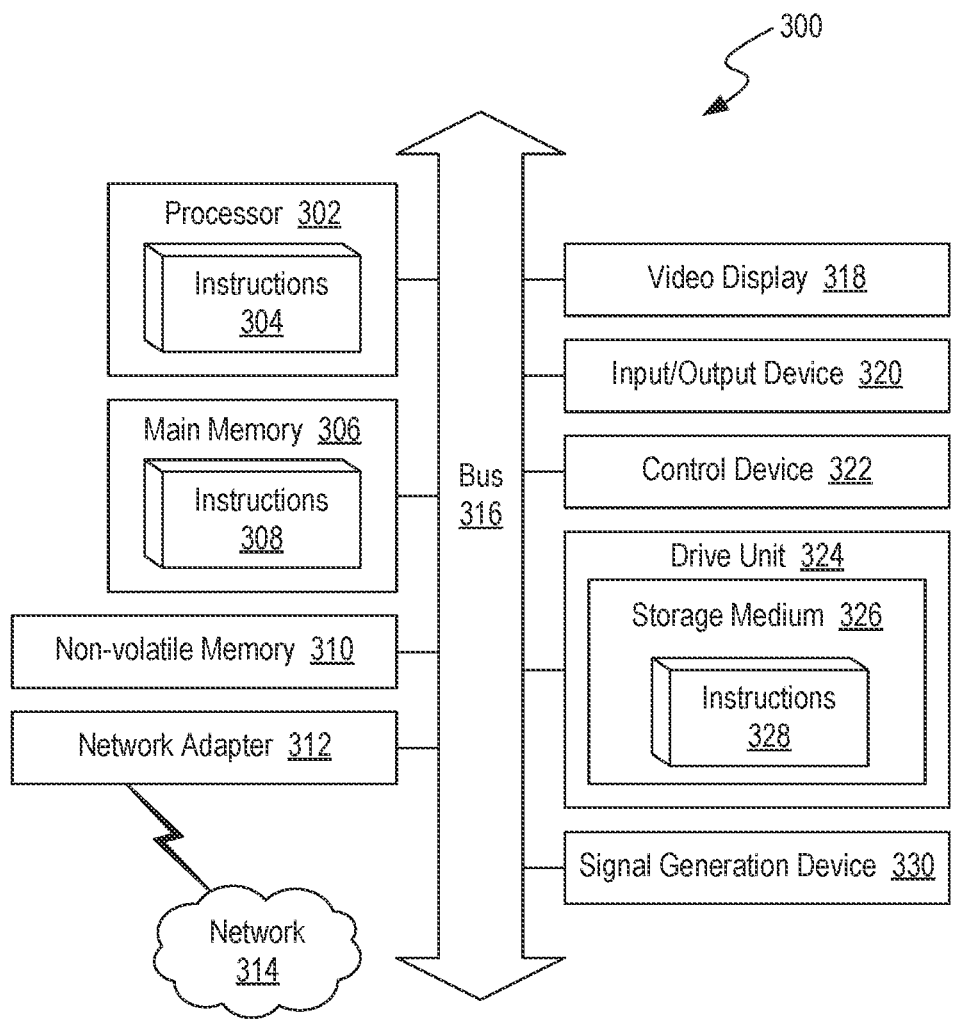
FIG. 3 is a block diagram illustrating an example computer system for surgical equipment monitoring, in accordance with one or more embodiments.

FIG. 3 is a block diagram illustrating an example computer system for surgical equipment monitoring, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the machine learning system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 330 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C)

bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality system (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMs), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multi-layer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4:
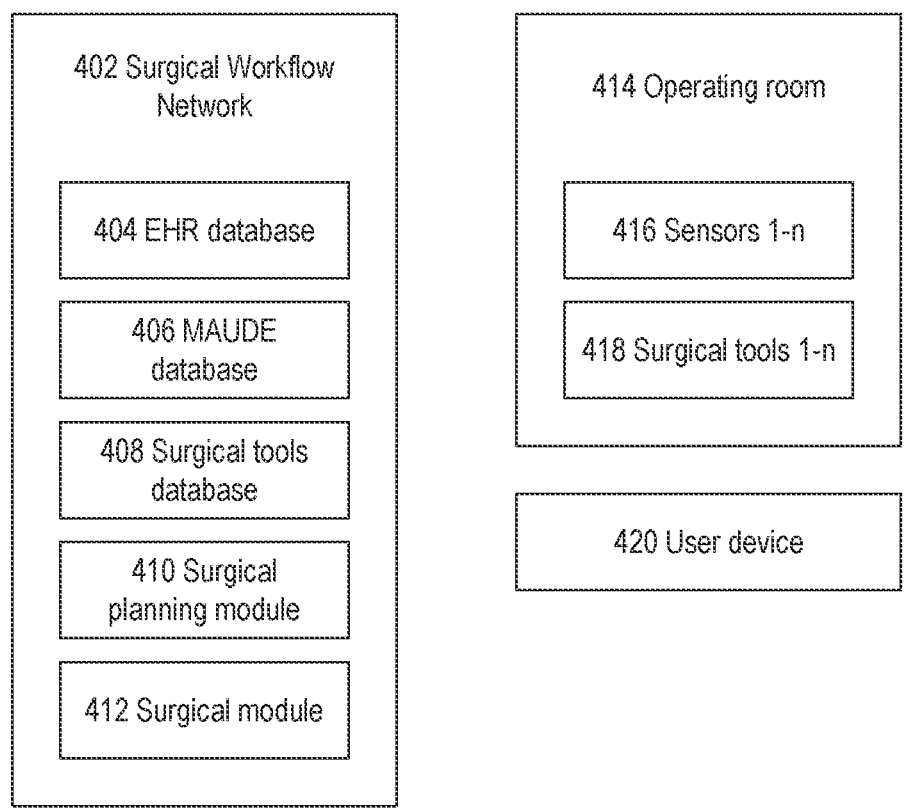
FIG. 4 is a block diagram illustrating an example environment for surgical equipment monitoring, in accordance with one or more embodiments.

FIG. 4 is a block diagram illustrating an example environment 400 for surgical equipment monitoring, in accordance with one or more embodiments. The environment 400 includes a surgical workflow network 402 that monitors surgical tools 418 and sensors 416 in an operating room 414 during a surgical procedure. The surgical workflow network 402 is a computer system, such as a server, computer, or tablet, etc., implemented using components of the example computer system 300 illustrated and described in more detail with reference to FIG. 3. In some embodiments, the surgical workflow network 402 is the same as or similar to the console 108 illustrated and described in more detail with reference to FIG. 1. The surgical tools 418 are the same as or similar to the tools of the surgical tower 128 and/or the surgical tools 154 illustrated and described in more detail with reference to FIG. 1. The sensors 416 are the same as or similar to the monitors 112 and/or the sensors 134 illustrated and described in more detail with reference to FIG. 1. The operating room 414 is the same as or similar to the operating room 102 illustrated and described in more detail with reference to FIG. 1. Likewise, embodiments can include different and/or additional components, or the components can be connected in different orders.

Surgical procedures typically require a sterile field. In some embodiments, the sterile field maintained in the operating room 414 is in a medical care facility, such as a hospital, a doctor's office, or an outpatient surgery center. An example doctor's office 110 is illustrated and described in more detail with reference to FIG. 1. In the operating room 414, there are some numbers 1 through n of the sensors 416. The sensors 416, such as microphones or optical sensors, can be associated with one or more areas in the operating room 414. The sensors 416 can further be associated with measuring a specific parameter of the patient, such as respiratory rate, blood pressure, blood oxygen level, heart rate, etc.

In some embodiments, the surgical workflow network 402 is communicatively coupled to the surgical tools 418 and the sensors 416 in the operating room 414 over a direct connection, such as Ethernet, or wirelessly by the cloud or a local connection. A network connection is implemented using the network adapter 312 and the network 314 illustrated and described in more detail with reference to FIG. 3. The surgical workflow network 402 includes an electronic health records (EHR) database 404 that contains patient records. The EHR database 404 is the same as or similar to the EHR database 106 illustrated and described in more detail with reference to FIG. 1. Electronic health records are a digital version of a patient's paper chart. The EHR database 404 includes more information than a traditional patient chart, including, but not limited to, the patient's medical history, diagnoses, medications, treatment plans, allergies, diagnostic imaging, lab results, etc. In some embodiments, the steps for each surgical procedure are stored in the EHR database 404.

The surgical workflow network 402 includes or has external access to a U.S. Food and Drug Administration (FDA) Manufacturer and User Facility Device Experience (MAUDE) database 406. The MAUDE database 406 represents reports of adverse events involving medical devices. The database includes information on medical devices that may have malfunctioned or caused a death or serious injury. In some embodiments, this data is used to identify surgical procedures and surgical steps in surgical procedures at which adverse events related to a specific surgical tool have previously occurred. While the MAUDE database 406 is maintained by the U.S. FDA, the data is available from jurisdictions outside the United States and is also available from other regulatory agencies, device manufacturers, or academic/medical research facilities.

The surgical workflow network 402 includes a surgical tools database 408 that contains data related to characteristics and use of the surgical tools 418. The characteristics can include specifications for the surgical tools 418, surgical procedures in which the surgical tools 418 are used, consumables used by the surgical tools 418, the sensors the surgical tools 418 include, and specified operating parameters for the surgical tools 418. The consumables used by the surgical tools 418 are the same as or similar to the consumables 158 illustrated and described in more detail with reference to FIG. 1. Surgical procedures sometimes require one or more surgical tools 418, such as scalpels, cauterizers, staplers, retractors, etc. In some embodiments, one or more surgical tools 418 have one or more integrated sensors 416. For example, a surgical stapler can have a force transducer on the left and right sides of the anvil to determine if a staple has been properly formed.

The sensors included by the surgical tools 418 are the same as or similar to the sensors 134 illustrated and described in more detail with reference to FIG. 1. For example, a linear cutting surgical stapler model used in abdominal, gynecological, or thoracic surgeries is compatible with three types of surgical staples and has two force transducers in the anvil to measure the pressure placed on either side of the staple. In some embodiments, the surgical tools database 408 includes data related to specific operational parameters for a given surgical tool 418 at a given step in a specific surgical procedure. For example, a surgical stapler model uses seven 45 mm wide staples that have a closed staple height of 2.3 mm, which includes 0.2 mm of buttress material to close the fundus of a male patient in Step 12 of a one anastomosis gastric bypass procedure. The surgical tools database 408 can also indicate that the stapler's force transducers should register 1.9 lbs. of pressure when forming the staples.

The surgical workflow network 402 includes a surgical planning module 410 that enables practitioners, such as doctors, nurses, medical equipment technicians, or hospital administrators to plan a surgical procedure. In some embodiments, a portion or all of the planning is performed by the robotic surgical system 160 illustrated and described in more detail with reference to FIG. 1. The surgical planning module 410 is implemented in computer hardware, software, or a combination thereof using components of the example computer system 300 illustrated and described in more detail with reference to FIG. 3. The surgical steps, medical supplies, and surgical tools 418 needed for a surgical procedure are input through the surgical planning module 410 and recorded in the EHR database 404. The surgical steps, medical supplies, and surgical tools 418 needed for a surgical procedure are sometimes referred to as a surgical workflow.

The surgical workflow network 402 monitors a surgical tool being used to perform a surgical procedure. In some embodiments, the surgical workflow network 402 receives a message that a medical practitioner is initiating the surgical procedure. The message can be a text message, an audible alert, a digital signal, an image displayed on a screen, etc., that the surgical workflow network 402 can receive and act upon. The message can be received from at least one of an optical sensor detecting a patient in the operating room 414, a barcode scanner that reads a patient's ID bracelet, or a microphone detecting an audio cue. Monitoring the surgical tool is performed responsive to receiving the message. For example, the surgical workflow network 402 includes a surgical module 412 that monitors the sensors 416 and the surgical tools 418 in the operating room 414 during a surgical procedure to identify instances of the misuse or malfunction of a surgical tool 418 that can result in an adverse event. The surgical module 412 can notify a doctor of the potential adverse event and adjust a workflow plan for the surgical procedure in the EHR database 404. The surgical module 412 is implemented in computer hardware, software, or a combination thereof using components of the example computer system 300 illustrated and described in more detail with reference to FIG. 3. For example, the force transducers in a surgical stapler can register asymmetry in the force applied to either side of a surgical staple in the forming of that staple. The asymmetry can be indicative of a malformed staple, which indicates a surgical complication. Upon detection of the asymmetry, the surgical module 412 notifies a doctor of the malformed staple. The doctor can then adjust the surgical procedure steps, such as switching from staples to sutures, specified by the doctor using the surgical planning module 410. In some embodiments, a portion or all of the adjustment is performed by the robotic surgical system 160 illustrated and described in more detail with reference to FIG. 1. Sutures are described in more detail with reference to FIG. 1. The modified surgical procedure steps can be recorded in the EHR database 404.

In some embodiments, a doctor modifies surgical steps suggested to him based on an observed error, or a notification from the surgical module 412 or the surgical planning module 410. For example, the surgical workflow network 402 generates a notification indicating a potential adverse event. The surgical workflow network 402 sends the notification to the user device 420, which is communicably coupled to the surgical workflow network 402. The surgical workflow network 402 can modify a surgical plan of the surgical procedure to avoid the adverse event. The surgical plan is accessible from the user device 420 for performing the surgical procedure. In some embodiments, a portion or all of the modification is performed by the robotic surgical system 160 illustrated and described in more detail with reference to FIG. 1. For example, an amount of a given sensor measurement can vary from the expected value in the surgical tools database 408. The expected value can be specified by a device manufacturer, regulatory agencies, medical practitioners, hospital administrators, or by an algorithm of the robotic surgical system 160. For example, a doctor may only be notified of asymmetry in the force applied to the two sides of a surgical staple if there is a greater than 50% difference in the force applied to one side versus the other. The doctor may not be notified of a malformed staple and instead only be notified if more than 3 in 10 staples are malformed, or when 2 adjacent staples are malformed because there is little risk for surgical complications related to the use of surgical staples in closing this type of tissue in the respective location in the patient.

In some embodiments, the surgical workflow network 402 determines that an adverse event is associated with the surgical tool when used for the surgical procedure from the MAUDE database 406. The MAUDE database 406 is used to identify specific steps in a surgical procedure during which a surgical tool 418, such as a given model of a surgical stapler, has had adverse events reported. In some embodiments, the surgical workflow network 402 detects a malfunction of a surgical tool or misuse of the surgical tool from the surgical tools database 408. The malfunction or misuse is associated with an adverse event. In some embodiments, detecting the malfunction or misuse includes determining that a measurement by a sensor varies from an expected value in the surgical tools database 408 by less than a threshold when the surgical workflow network 402 determines that the adverse event is associated with a current surgical step of the surgical procedure from the MAUDE database 406. Even when a given sensor measurement varies a smaller amount from the expected value in the surgical tools database 408, the variation may be problematic during a surgical step that has had adverse events recorded. For example, while a doctor may only be notified if more than 3 in 10 staples are malformed during a low-risk step in a surgical procedure, he may be notified when a single staple is malformed during a high-risk surgical step because that staple is proximal to an artery, thus increasing the risk of bleeding if there is a malfunction or misuse of the stapler in that surgical step. A high-risk surgical step is one for which the likelihood of an adverse event resulting is greater than a threshold. For example, for a high-risk surgical step, the likelihood of an adverse event resulting can be 70%, 90%, or 99%, etc. The threshold for what is considered a malformed staple can also change based on the surgical context. For example, a staple can be considered malformed when there is only a 25% difference in the force applied to either side of the staple during the forming of that staple.

In some embodiments, a user device 420 is communicatively coupled to the surgical workflow network 402. The user device 420 is a computer device, such as a computer, tablet, smartphone, smart speaker, etc., implemented using components of the example computer system 300 illustrated and described in more detail with reference to FIG. 3. In some embodiments, the user device 420 is the same as or similar to the console 108 illustrated and described in more detail with reference to FIG. 1. Through the user device 420, a user (e.g., a doctor, nurse, medical equipment technician) can access the surgical planning module 410 and the surgical module 412. A person skilled in the art will recognize that more than one user device 420 can be involved in a single surgical procedure. For example, a doctor can plan a surgery using a computer terminal but interact with the surgical module 412 using a smart speaker in the operating room 414.

In additional embodiments, the surgical workflow network 402 is part of a robotic surgical system being used to perform the surgical procedure. An example robotic surgical system 160 is illustrated and described in more detail with reference to FIG. 1. In other embodiments, the surgical workflow network 402 transmits the surgical plan to the robotic surgical system being used to perform the surgical procedure. In some embodiments, a computer-implemented method of modifying a surgical plan based on potential adverse events includes monitoring, via the one or more sensors 416, at least a portion of a surgical procedure performed by the robotic surgical system using a surgical tool 418 according to a surgical plan. A potential adverse surgical event associated with the surgical tool 418 is identified based on the monitoring and surgical tool data from a medical device reports (MDRs) database. The MDRs database can be the MAUDE database 406 or a separate database stored by the surgical workflow network 402 or by the console 108 illustrated and described in more detail with reference to FIG. 1. Modification of the surgical plan is caused based on the identified potential adverse surgical event.

In some embodiments, specific surgical tools for the surgical procedure are identified. Surgical tool data for the identified specific surgical tools is retrieved from the MAUDE database 406. The retrieved surgical tool data is stored in the MDRs database, wherein the retrieved surgical tool data includes data for the surgical tool 418 that is monitored. In some embodiments, the surgical procedure is simulated to predict adverse surgical events using data from the MDRs database. The surgical plan is generated based, at least partly, on the simulation. In some embodiments, it is determined whether a predicted adverse surgical event is the potential adverse surgical event for surgical plan modification. In some embodiments, one or more records are identified from the MAUDE database 406 based on the surgical procedure, the surgical tool, or both. Data from the one or more records is identified for identifying the potential adverse surgical event. In some embodiments, one or more surgical complications associated with the potential adverse surgical event are classified. In some embodiments, in response to the identified potential adverse surgical event being malfunctioning of the surgical tool, another surgical tool is used to perform at least one surgical step planned for the malfunctioning surgical tool.

In some embodiments, a notification of a surgical complication is sent. The surgical plan is modified with at least one corrective surgical step for the surgical complication. In some embodiments, machine vision is used to determine whether the potential adverse surgical event occurred. In some embodiments, the MDRs database is updated with data collected during the surgical procedure. In some embodiments, the surgical plan is stored in the EHR database 404, wherein the surgical plan specifies multiple surgical steps for the surgical procedure, at least one medical supply used in the surgical procedure, and/or the surgical tool 418. In some embodiments, a surgical system database is used to identify the potential adverse event. The surgical system database describes maintenance of the robotic surgical system 160, specifications of the robotic surgical system 160, specifications of the surgical tool 418, surgical procedures for the surgical tool 418, at least one consumable used by the surgical tool 418, operational parameters for the surgical tool 418, or at least one sensor 416 configured to monitor the surgical tool 418.

In some embodiments, an adverse event notification is sent to a manufacturer of the surgical tool 418. In some embodiments, the surgical tool 418 is manipulated by a robotic arm of the robotic surgical system 160, wherein the one or more sensors 416 are part of the surgical tool 418, the robotic arm, or both. In some embodiments, identifying the potential adverse surgical event includes determining that a sensor measurement from the one or more sensors 416 differs from an expected value in the surgical tools database 408 by greater than a tool-specific threshold. In some embodiments, the potential adverse surgical event is identified by determining that a measurement by the one or more sensors 416 differs from a reference value in the surgical tools database 408 by less than a predetermined threshold. It is determined that the potential adverse surgical event is associated with a current surgical step of the surgical procedure. In some embodiments, a measurement by at least one sensor associated with the surgical tool 418 is compared to a reference value. It is determined whether a high-risk threshold indicating the potential adverse surgical event has been met based on comparing the measurement to the expected value. In some embodiments, determining whether the high-risk threshold has been met includes determining that the measurement by the at least one sensor varies from the expected value by greater than the high-risk threshold.

FIG. 5 is a table illustrating an example manufacturer and user facility device experience (MAUDE) database 500, in accordance with one or more embodiments. The MAUDE database 500 is the same as or similar to the MAUDE database 406 illustrated and described in more detail with reference to FIG. 4. The MAUDE database includes medical device reports (MDRs) submitted by medical device manufacturers, importers, and device user facilities. The MDRs describe adverse events associated with surgical tools or surgical steps. The U.S. Food and Drug Administration (FDA) typically receives MDRs whenever a medical device is suspected of malfunctions or associated with injuries or death. The MAUDE database 500 is a public repository of the MDRs submitted by medical device manufacturers, importers, and device user facilities, who are typically required to submit these reports. The U.S. FDA also receives MDRs from voluntary reporters such as patients, practitioners, and consumers. An MDR can include information about the suspected device type, manufacturer, model, procedure, patient problem, and event description.

FIG. 6A is a table illustrating an example surgical tools database, in accordance with one or more embodiments. The surgical tools database is the same as or similar to the surgical tools database 408 illustrated and described in more detail with reference to FIG. 4. The surgical tools database can contain data related to one or more surgical tools 418 or other types of medical devices used in a surgical procedure. The one or more surgical tools 418 are illustrated and described in more detail with reference to FIG. 4. In some embodiments, the surgical tools database describes at least one of specifications of a surgical tool, surgical procedures in which the surgical tool is used, at least one consumable used by the surgical tool, or operational parameters for the surgical tool. Likewise, embodiments can include different and/or additional components, or the components can be connected in different orders.

In some embodiments, the surgical tools database describes at least one sensor used by the surgical tool. Monitoring the surgical tool includes monitoring the at least one sensor during the surgical procedure. For example, the database can include, but is not limited to, make, model, type, surgical procedures a surgical tool 418 is used in, the sensors 416 related to the surgical tool 418, the standard measurements from those sensors 416 for a given step in a given surgical procedure's workflow, etc. The sensors 416 are illustrated and described in more detail with reference to FIG. 4. In some embodiments, a surgical tool in use is a stapler, the at least one sensor is a pair of force transducers, and the operational parameters include an amount of pressure registered by the force transducers.

For example, a model of a circular stapler can be used in a one anastomosis gastric bypass. The force transducers are expected to measure 2 pounds (lbs.) of pressure each. If a step is a high-risk surgical step, which can be associated with an MDR in the MAUDE database 406 for that surgical procedure, workflow step, or surgical tool 418, the threshold for notifying a surgeon can be any difference in the pressure readings between the two force transducers that exceed 25%. A high-risk surgical step is one for which the likelihood of an adverse event resulting is greater than a threshold. For example, for a high-risk surgical step, the likelihood of an adverse event resulting can be 70%, 90%, or 99%, etc. The MAUDE database 406 is illustrated and described in more detail with reference to FIG. 4. The difference in the pressure readings can indicate a malformed staple. In a low-risk surgical step associated with the absence of any related MDRs in the MAUDE database 406, the threshold for notifying a surgeon can be 3 malformed staples in 10, or 2 adjacent malformed staples, with the threshold for a malformed staple being a difference in the pressure reading between the two force transducers that exceeds 50%. A low-risk surgical step is one for which the likelihood of an adverse event resulting is less than a threshold. For example, for a low-risk surgical step, the likelihood of an adverse event resulting can be 10%, 1%, or 0.1%, etc.

FIG. 6B illustrates an example set of acceptable and unacceptable staple forms, in accordance with one or more embodiments. An optical sensor can compare a formed staple to the set of acceptable and unacceptable staple forms. The comparison can be made by object recognition. The object recognition is performed using, for example, the machine learning system 200 illustrated and described in more detail with reference to FIG. 2. For example, images of the staple can be used as the input data 204 shown in FIG. 2, while the set of acceptable and unacceptable staple forms can be used as the training data 220 shown in FIG. 2.

Figure 7:
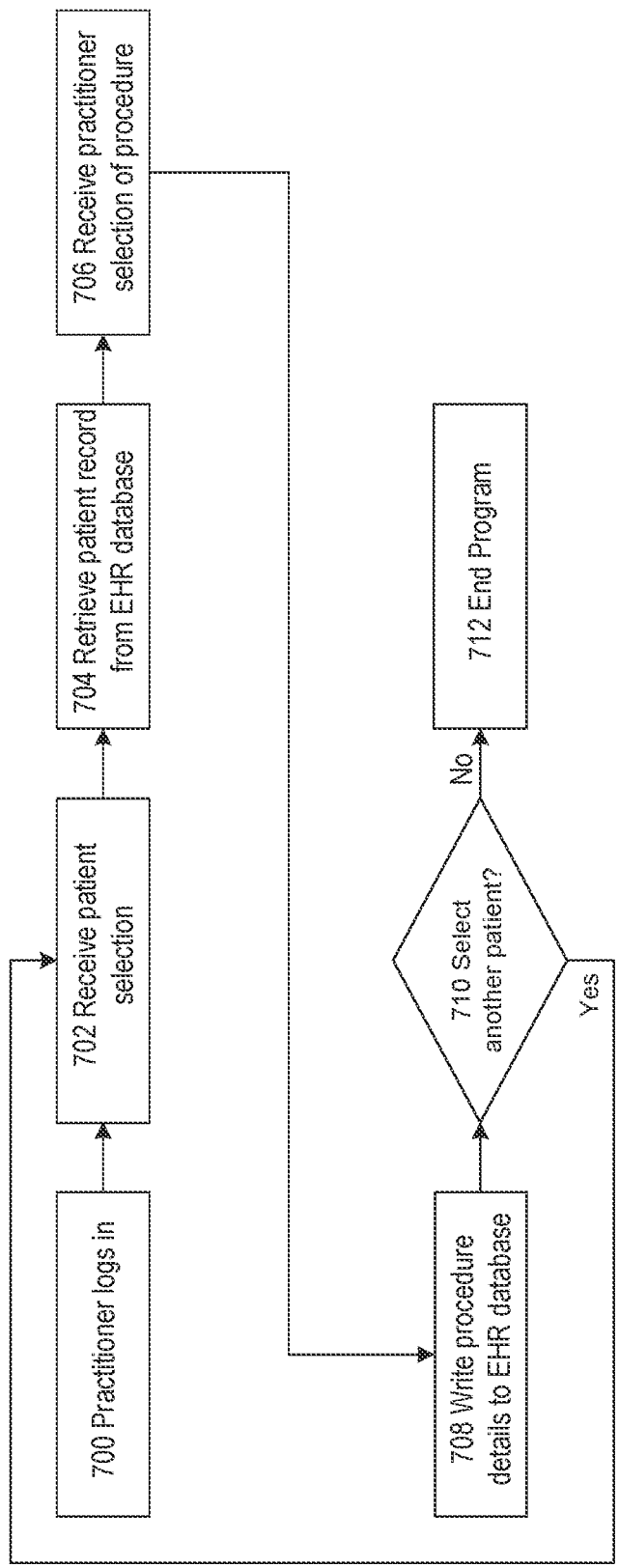
FIG. 7 is a flow diagram illustrating an example process for surgical equipment monitoring, in accordance with one or more embodiments.

FIG. 7 is a flow diagram illustrating an example process for surgical equipment monitoring, in accordance with one or more embodiments. In some embodiments, the process is performed by the surgical planning module 410 illustrated and described in more detail with reference to FIG. 4. In other embodiments, the process of FIG. 7 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 700, the surgical planning module 410 receives information that a medical practitioner, typically a doctor performing a surgical procedure, has logged in to the surgical workflow network 402. The surgical workflow network 402 is illustrated and described in more detail with reference to FIG. 4. The information is received from the user device 420 illustrated and described in more detail with reference to FIG. 4. In step 702, the surgical planning module 410 receives information indicating a selection of a patient for the surgical procedure from the medical practitioner. The information is received from the user device 420. In step 704, the surgical planning module 410 retrieves the selected patient's electronic health records from the EHR database 404. The EHR database 404 is illustrated and described in more detail with reference to FIG. 4.

In some embodiments, the surgical workflow network 402 generates a surgical plan. The surgical plan specifies multiple surgical steps of the surgical procedure, at least one medical supply used in the surgical procedure, and a surgical tool to be used. The surgical workflow network 402 stores the surgical plan in the EHR database 404. For example, in step 706, the surgical planning module 410 receives information from the medical practitioner indicating a selection of a particular surgical procedure that the selected patient is to undergo. In step 708, the surgical planning module 410 transmits to or stores in the EHR database 404 the details of the particular surgical procedure, including the surgical tools 418 to be used in each of the surgical procedure steps. The details of the particular surgical procedure are sometimes referred to as a surgical workflow. The surgical tools 418 are illustrated and described in more detail with reference to FIG. 4. In step 710, the surgical planning module 410 determines whether the medical practitioner is selecting another patient record from the EHR database 404. If the surgical planning module 410 determines that the medical practitioner is selecting another patient record, the surgical planning module 410 returns to step 702. If the surgical planning module 410 determines that the medical practitioner is not selecting another patient record, the surgical planning module 410 terminates the session in step 712.

Figure 8:
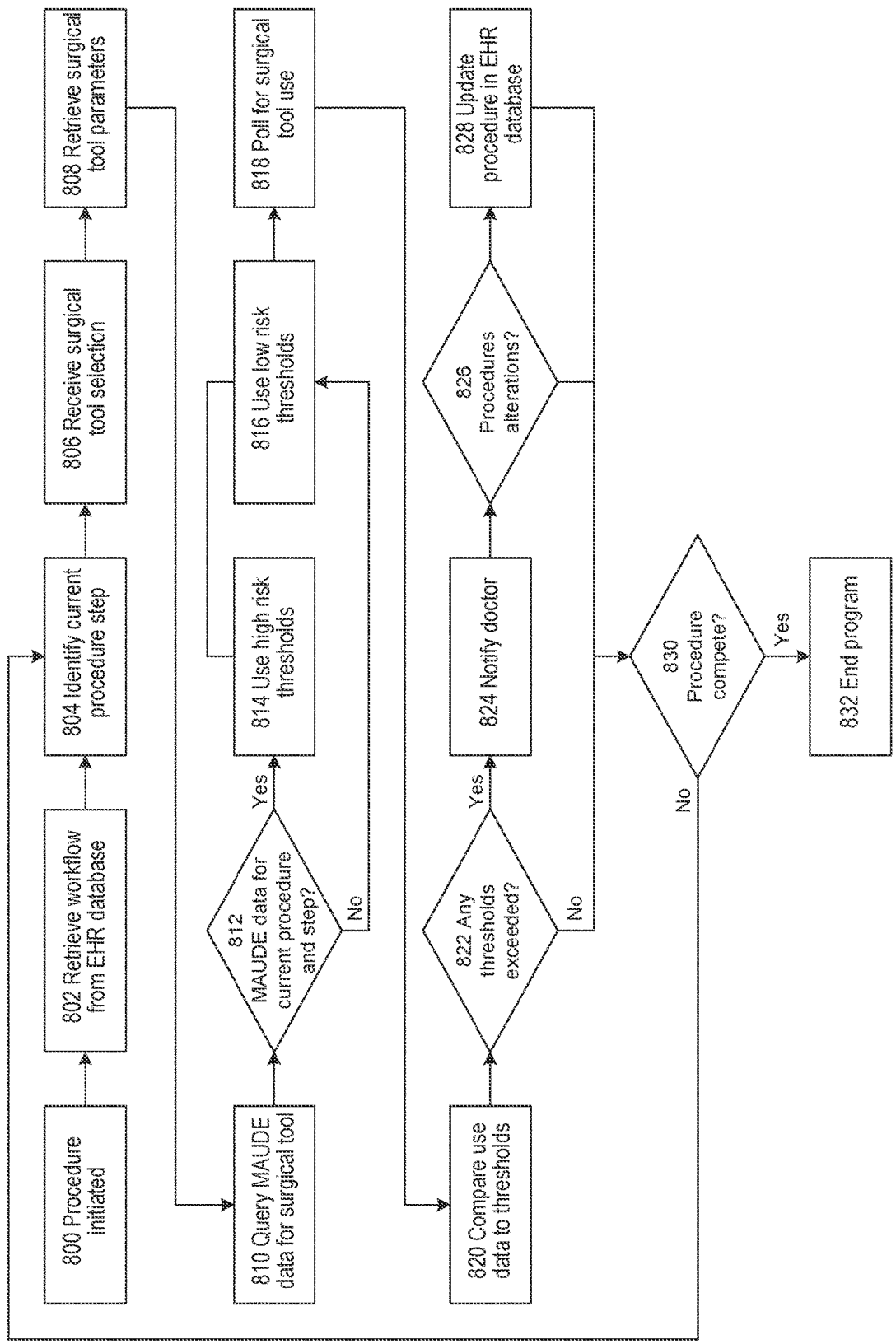
FIG. 8 is a flow diagram illustrating an example process for surgical equipment monitoring, in accordance with one or more embodiments.

FIG. 8 is a flow diagram illustrating an example process for surgical equipment monitoring, in accordance with one or more embodiments. In some embodiments, the process is performed by the surgical module 412 illustrated and described in more detail with reference to FIG. 4. In other embodiments, the process of FIG. 8 is performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps, or perform the steps in different orders.

In step 800, the surgical module 412 initiates a session. In some embodiments, the surgical module 412 receives information that a medical practitioner is initiating a surgical procedure from the user device 420. The user device 420 is illustrated and described in more detail with reference to FIG. 4. In other embodiments, the surgical module 412 receives information that a medical practitioner is initiating a surgical procedure from a trigger device detected by one or more sensors 416 in the operating room 414. The one or more sensors 416 and the operating room 414 are illustrated and described in more detail with reference to FIG. 4. For example, an optical sensor can detect a patient being brought into the operating room 414. In another example, a barcode scanner reads a patient's ID bracelet or a microphone detects an audio cue to initiate the surgical procedure. In another example, a doctor states to a smart speaker, "Beginning one anastomosis gastric bypass procedure on patient John Doe." In some embodiments, the surgical workflow network 402 includes a device that receives doctors' audio commands and translates the commands to digital data to be used in the surgical procedure. The device can be part of the robotic surgical system 160 illustrated and described in more detail with reference to FIG. 1.

In some embodiments, the surgical module 412 retrieves a surgical plan from the EHR database 404. The surgical module 412 identifies a current step of the surgical plan using at least one of an optical sensor detecting a practitioner performing the current step or a microphone detecting an audio cue describing the current step. For example, in step 802, the surgical module 412 retrieves electronic health records, including a surgical workflow specified using the surgical planning module 410, for the identified patient from the EHR database 404. The surgical planning module 410 and the EHR database 404 are illustrated and described in more detail with reference to FIG. 4. In step 804, the surgical module 412 identifies a current step of the retrieved surgical workflow. The current surgical step can be identified by one or more of the sensors 416, such as a verbal indication from a surgeon, a nurse, a technician, or an optical recognition system that produces output indicating, for example, that a clamp is being applied to a particular tissue type and location. The optical recognition system can be part of the robotic surgical system 160 and can be implemented using the machine learning system 200 illustrated and described in more detail with reference to FIG. 2.

In some embodiments, the surgical module 412 receives an indication that a surgical tool 418 has been selected. The indication is received from one or more sensors 416 in the operating room 414. The surgical module 412 retrieves operational parameters for the surgical tool 418 from the surgical tools database 408. For example, in step 806, the surgical module 412 receives information indicating selection of a surgical tool 418. In some embodiments, information indicating selection of a surgical tool 418 is received from the one or more sensors 416, similar to the information identifying a surgical step in a surgical workflow. In other embodiments, information indicating selection of a surgical tool 418 is received from a sensor 416 in the surgical tool 418 that has been selected. In step 808, after receiving information indicating selection of a surgical tool 418, the surgical module 412 retrieves parameters for that surgical tool 418 from the surgical tools database 408. The surgical tools database 408 is illustrated and described in more detail with reference to FIG. 4. In some embodiments, the surgical module 412 retrieves MDRs related to the surgical tool 418, the surgical procedure, or a current surgical step from the MAUDE database 406. For example, in step 810, the surgical module 412 queries the MAUDE database 406 to retrieve medical device reports (MDRs) related to the selected surgical tool 418, the present surgical procedure, and the current surgical workflow step. The MAUDE database 406 is illustrated and described in more detail with reference to FIG. 4.

In some embodiments, the surgical module 412 determines that there is an MDR related to the surgical tool 418. Responsive to determining that there is an MDR related to the surgical tool 418, the surgical module 412 retrieves high-risk thresholds from the surgical tools database 408. The high-risk thresholds are associated with measurements by at least one sensor used by the surgical tool 418. For example, in step 812, the surgical module 412 determines whether there is an MDR related to the selected surgical tool 418, the surgical procedure, or the surgical workflow step. In step 814, if there is an MDR related to the selected surgical tool 418, the surgical procedure, or the surgical workflow step, the surgical module 412 retrieves stored high-risk thresholds from the surgical tools database 408. In some embodiments, the surgical module 412 determines absence of an MDR related to the surgical tool 418. Responsive to determining absence of the MDR, the surgical module 412 retrieves low-risk thresholds from the surgical tools database 408. The low-risk thresholds are associated with measurements by at least one sensor used by the surgical tool 418. For example, in step 816, if there is no MDR related to the selected surgical tool 418, the surgical procedure, or the surgical workflow step, the surgical module 412 retrieves stored low-risk thresholds from the surgical tools database 408. In some embodiments, the surgical module 412 polls at least one sensor used by the surgical tool 418 for an indication of use of the surgical tool 418. The surgical module 412 receives measurements of the use of the surgical tool 418 from the at least one sensor. For example, in step 818, the surgical module 412 polls the surgical tool 418 and/or one or more sensors 416 for an indication of use of the selected surgical tool 418. For example, the surgical module 412 receives, from the polling, a measurement from the force transducers in the XYZ brand Circular Stapler model 456.

In some embodiments, the surgical module 412 compares a measurement by at least one sensor used by a surgical tool 418 to an expected value in the surgical tools database 408. The surgical module 412 determines whether a high-risk threshold indicating the adverse event has been met based on comparing the measurement to the expected value. For example, in step 820, the surgical module 412 compares the data received in step 818 to an expected measurement and the identified thresholds. For example, the two force transducers are expected to record equal measurements of 2 lbs. of force. However, the received measurements from one force transducer are 1.6 lbs. and the received measurements from the other force transducer are 2.2 lbs. of force.

In some embodiments, the surgical module 412 determines whether a high-risk threshold has been met by determining that the measurement by the at least one sensor varies from the expected value by greater than the high-risk threshold. For example, in step 820, the surgical module 412 determines whether any thresholds that can indicate a potential adverse event have been met. During a high-risk surgical step, the force transducers can receive measurements indicative of a potential adverse event. A high-risk surgical step is one for which the likelihood of an adverse event resulting is greater than a threshold. For example, for a high-risk surgical step, the likelihood of an adverse event resulting can be 70%, 90%, or 99%, etc. Continuing the example, an indication of an adverse event is based on a greater than 25% difference in the force transducer measurements in forming a staple. It can be indicative of an adverse event in a high-risk surgical step, when there is a single malformed staple, such as a staple near an artery. The same transducer measurements would not exceed the low-risk threshold of a greater than 50% difference in the two transducer measurements. For example, a single malformed staple may not, on its own, indicate an adverse event. There would need to be either 3 in 10 malformed staples or 2 adjacent malformed staples that meet the criteria for malformed staples.

In some embodiments, detecting malfunction or misuse includes determining that a measurement by a sensor varies from an expected value in the surgical tools database 408 by greater than a threshold. The surgical tools database 408 is illustrated and described in more detail with reference to FIG. 4. For example, an optical sensor of the one or more sensors 416 monitors the stapler's path and identifies when an actual path of the stapler diverges from an expected path. During a high-risk step, a threshold for notifying a doctor can be a 5 mm divergence from an expected path, while during a low-risk step, that threshold can be 15 mm. If no thresholds are met, the surgical module 412 proceeds to step 830. In step 824, the surgical module 412 generates a notification if one or more thresholds are met. The notification can be a text message, an audible notification, or a haptic indication to a doctor. In some embodiments, a notification is generated by a voice assistant that alerts a doctor that a threshold is being met. The doctor can consider altering the surgical workflow to assess a patient's status and surgical tool parameters, and determine whether corrective action is needed.

In step 826, the surgical module 412 receives information indicating whether a doctor has decided to modify the surgical workflow for the current surgical procedure. The surgical workflow for the current surgical procedure is stored in the EHR database 404. The EHR database 404 is illustrated and described in more detail with reference to FIG. 4. If the surgical module 412 receives information indicating that the doctor does not wish to alter the surgical workflow, the surgical module 412 proceeds to step 830. In step 826, if the surgical module 412 receives information indicating that the doctor wishes to alter the surgical workflow, the surgical module 412 stores the change in the surgical workflow in the EHR database 404 in step 828. For example, upon receiving a malformed staple notification in a high-risk step, a doctor can switch the surgical procedure from staples to sutures. In some embodiments, a doctor removes a malformed staple based, at least in part, on the notification. In other embodiments, a doctor is alerted to a hemorrhage; the doctor modifies the surgical procedure to begin surgery from a planned arthroscopic procedure. In step 830, the surgical module 412 determines whether the surgical procedure is complete. If the surgical procedure is not complete, the surgical module 412 returns to step 804. If the surgical procedure is complete, the surgical module 412 terminates the session in step 832.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example, using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, and no special significance is to be placed upon whether or not a term is elaborated or discussed herein. Synonyms for certain terms are provided. A recital of one or more synonyms does not exclude the use of other synonyms. The use of examples anywhere in this specification including examples of any term discussed herein is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

What is claimed is:

1. A computer-implemented method of modifying a surgical plan based on a potential adverse surgical event, the method comprising:
monitoring, using one or more sensors, at least a portion of a surgical procedure performed by a surgical robot using a surgical tool according to the surgical plan; and
determining, based on the monitoring, the potential adverse surgical event using at least one machine learning model trained to identify malfunctioning of the surgical tool based on surgical tool data from a medical device reports (MDRs) database,
wherein the potential adverse surgical event is associated with the surgical tool;
identifying, using the at least one machine learning model, another surgical tool to perform at least one surgical step indicated by the surgical plan for the malfunctioning surgical tool; and
performing the at least one surgical step using the other surgical tool by the surgical robot.

2. The method of claim 1, comprising:
retrieving the surgical plan from an electronic health records (EHR) database; and
determining the at least one surgical step from the surgical plan using at least one of an optical sensor detecting a practitioner performing a current step or a microphone detecting an audio cue describing the current step.

3. The method of claim 1, comprising:
receiving, from the one or more sensors, an indication that the surgical tool has been selected by the surgical robot; and
retrieving operational parameters for the surgical tool from the MDRs database.

4. The method of claim 1, comprising:
retrieving MDRs related to at least one of the surgical tool, the surgical procedure, or the at least one surgical step from the MDRs database.

5. The method of claim 1, comprising:
determining that there is an MDR related to the surgical tool; and
responsive to determining that there is an MDR related to the surgical tool, retrieving, from the MDRs database, high-risk thresholds associated with measurements by at least one sensor used by the surgical tool.

6. The method of claim 1, comprising:
determining absence of an MDR related to the surgical tool; and
responsive to determining absence of the MDR, retrieving, from the MDRs database, low-risk thresholds associated with measurements by at least one sensor used by the surgical tool.

7. The method of claim 1, comprising:
polling at least one sensor used by the surgical tool for an indication of use of the surgical tool; and
receiving measurements of the use of the surgical tool from the at least one sensor.

8. A non-transitory computer-readable storage medium storing computer instructions, which when executed by one or more computer processors, cause the one or more computer processors to:
monitor, using one or more sensors, at least a portion of a surgical procedure performed by a surgical robot using a surgical tool according to a surgical plan; and
determine, based on the monitoring, a potential adverse surgical event using at least one machine learning model trained to identify malfunctioning of the surgical tool based on surgical tool data from a medical device reports (MDRs) database,
wherein the potential adverse surgical event is associated with the surgical tool;
identify, using the at least one machine learning model, another surgical tool to perform at least one surgical step indicated by the surgical plan for the malfunctioning surgical tool; and
perform the at least one surgical step using the other surgical tool by the surgical robot.

9. The storage medium of claim 8, wherein the computer instructions cause the one or more computer processors to:
retrieve the surgical plan from an electronic health records (EHR) database; and
determine the at least one surgical step from the surgical plan using at least one of an optical sensor detecting a practitioner performing a current step or a microphone detecting an audio cue describing the current step.

10. The storage medium of claim 8, wherein the computer instructions cause the one or more computer processors to:
receive, from the one or more sensors, an indication that the surgical tool has been selected by the surgical robot; and
retrieve operational parameters for the surgical tool from the MDRs database.

11. The storage medium of claim 8, wherein the computer instructions cause the one or more computer processors to:
retrieve MDRs related to at least one of the surgical tool, the surgical procedure, or the at least one surgical step from the MDRs database.

12. The storage medium of claim 8, wherein the computer instructions cause the one or more computer processors to:
determine that there is an MDR related to the surgical tool; and
responsive to determining that there is an MDR related to the surgical tool, retrieve, from the MDRs database, high-risk thresholds associated with measurements by at least one sensor used by the surgical tool.

13. The storage medium of claim 8, wherein the computer instructions cause the one or more computer processors to:
determine absence of an MDR related to the surgical tool; and
responsive to determining absence of the MDR, retrieve, from the MDRs database, low-risk thresholds associated with measurements by at least one sensor used by the surgical tool.

14. The storage medium of claim 8, wherein the computer instructions cause the one or more computer processors to:
poll at least one sensor used by the surgical tool for an indication of use of the surgical tool; and
receive measurements of the use of the surgical tool from the at least one sensor.

15. A system comprising:
one or more computer processors; and
a non-transitory computer-readable storage medium storing computer instructions, which when executed by the one or more computer processors, cause the one or more computer processors to:
monitor, using one or more sensors, at least a portion of a surgical procedure performed by a surgical robot using a surgical tool according to a surgical plan; and
determine, based on the monitoring, a potential adverse surgical event using at least one machine learning model trained to identify malfunctioning of the surgical tool based on surgical tool data from a medical device reports (MDRs) database, wherein the potential adverse surgical event is associated with the surgical tool;
identify, using the at least one machine learning model, another surgical tool to perform at least one surgical step indicated by the surgical plan for the malfunctioning surgical tool; and
perform the at least one surgical step using the other surgical tool by the surgical robot.

16. The system of claim 15, wherein the computer instructions cause the one or more computer processors to:
retrieve the surgical plan from an electronic health records (EHR) database; and
determine the at least one surgical step from the surgical plan using at least one of an optical sensor detecting a practitioner performing a current step or a microphone detecting an audio cue describing the current step.

17. The system of claim 15, wherein the computer instructions cause the one or more computer processors to:
receive, from the one or more sensors, an indication that the surgical tool has been selected by the surgical robot; and
retrieve operational parameters for the surgical tool from the MDRs database.

18. The system of claim 15, wherein the computer instructions cause the one or more computer processors to:
retrieve MDRs related to at least one of the surgical tool, the surgical procedure, or the at least one surgical step from the MDRs database.

19. The system of claim 15, wherein the computer instructions cause the one or more computer processors to:
determine that there is an MDR related to the surgical tool; and
responsive to determining that there is an MDR related to the surgical tool, retrieve, from the MDRs database, high-risk thresholds associated with measurements by at least one sensor used by the surgical tool.

20. The system of claim 15, wherein the computer instructions cause the one or more computer processors to:
determine absence of an MDR related to the surgical tool; and
responsive to determining absence of the MDR, retrieve, from the MDRs database, low-risk thresholds associated with measurements by at least one sensor used by the surgical tool.

* * * * *